(12) United States Patent
Cohen et al.

(10) Patent No.: US 7,927,322 B2
(45) Date of Patent: Apr. 19, 2011

(54) BODY-ADHERING PERSONAL CARE PRODUCT

(75) Inventors: Bliss Elizabeth Cohen, Appleton, WI (US); Stephen Michael Campbell, Winneconne, WI (US); Garry Roland Woltman, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 143 days.

(21) Appl. No.: 11/452,037

(22) Filed: Jun. 13, 2006

(65) Prior Publication Data
US 2007/0287973 A1 Dec. 13, 2007

(51) Int. Cl.
*A61F 13/15* (2006.01)
(52) U.S. Cl. ....... 604/385.03; 604/385.05; 604/385.101; 604/385.201; 604/387; 604/385.17
(58) Field of Classification Search ........ 604/385.02–385.05, 385.13, 385.201, 604/387, 385.101, 385.17
See application file for complete search history.

(56) References Cited

U.S. PATENT DOCUMENTS

| | | | |
|---|---|---|---|
| 2,742,903 A | 4/1956 | Lightner | |
| 3,906,952 A | 9/1975 | Zamist | |
| 4,072,151 A | 2/1978 | Levine | |
| 4,608,047 A | 8/1986 | Mattingly | |
| 4,753,648 A | 6/1988 | Jackson | |
| 4,846,824 A * | 7/1989 | Lassen et al. | 604/385.17 |
| 4,917,675 A * | 4/1990 | Taylor et al. | 604/385.02 |
| 5,114,419 A | 5/1992 | Daniel et al. | |
| 5,429,630 A * | 7/1995 | Beal et al. | 604/385.04 |
| 5,445,627 A | 8/1995 | Mizutani et al. | |
| H1602 H | 10/1996 | Brock | |
| 5,569,230 A * | 10/1996 | Fisher et al. | 604/385.06 |
| 5,611,790 A | 3/1997 | Osborn, III et al. | |
| 5,618,281 A | 4/1997 | Betrabet et al. | |
| 5,618,282 A | 4/1997 | Schlangen | |
| 5,658,270 A | 8/1997 | Lichstein | |
| 5,683,375 A | 11/1997 | Osborn, III et al. | |
| 5,800,654 A | 9/1998 | Davis et al. | |
| 5,807,367 A | 9/1998 | Dilnik et al. | |
| 6,033,391 A | 3/2000 | Osborn, III et al. | |
| 6,045,900 A | 4/2000 | Haffner et al. | |
| 6,156,818 A | 12/2000 | Corzani et al. | |
| 6,213,993 B1 | 4/2001 | Zacharias et al. | |

(Continued)

FOREIGN PATENT DOCUMENTS
AU 2005/100460 A4 6/2005
(Continued)

*Primary Examiner* — Jacqueline F. Stephens
(74) *Attorney, Agent, or Firm* — Bryan R. Rosiejka; David J. Arteman; Ralph H. Dean, Jr.

(57) ABSTRACT

The present invention provides an absorbent article having longitudinal direction, a lateral direction, a second portion and a first portion. This absorbent article has a topsheet which has a first major surface that forms a body-facing surface. In addition, the absorbent article has a backsheet which has a second major surface disposed distally from the first major surface. The second major surface of the backsheet forms a garment facing surface of the absorbent article. On the second portion of the top sheet on the first major surface, a body adhesive is applied. In the first portion of the absorbent article, a garment attachment device for attaching the absorbent article to an undergarment of a user is present.

9 Claims, 11 Drawing Sheets

U.S. PATENT DOCUMENTS

| | | |
|---|---|---|
| 6,254,582 B1 * | 7/2001 | O'Donnell et al. ...... 604/385.05 |
| 6,284,261 B1 | 9/2001 | Tramontana |
| 6,316,524 B1 | 11/2001 | Corzani et al. |
| 6,391,011 B1 | 5/2002 | Davis et al. |
| 6,497,692 B1 | 12/2002 | Tameishi et al. |
| 6,544,642 B2 | 4/2003 | Cinelli et al. |
| 6,613,955 B1 | 9/2003 | Lindsay et al. |
| 6,617,490 B1 | 9/2003 | Chen et al. |
| 6,620,143 B1 | 9/2003 | Zacharias et al. |
| 6,710,099 B2 | 3/2004 | Cinelli et al. |
| 6,824,535 B2 | 11/2004 | Kõ-Lby Falk |
| 2002/0058921 A1 * | 5/2002 | Sigl ........................ 604/385.201 |
| 2003/0120235 A1 | 6/2003 | Boulanger |
| 2004/0147892 A1 | 7/2004 | Mizutani et al. |
| 2004/0158221 A1 | 8/2004 | Mizutani et al. |
| 2004/0167491 A1 | 8/2004 | Mizutani |
| 2004/0178104 A1 | 9/2004 | Mizutani et al. |
| 2005/0008682 A1 | 1/2005 | Tramontana |
| 2005/0145523 A1 | 7/2005 | Zander et al. |
| 2007/0179466 A1 * | 8/2007 | Tremblay et al. ........ 604/385.02 |

FOREIGN PATENT DOCUMENTS

| | | |
|---|---|---|
| DE | 2930929 A1 * | 2/1981 |
| EP | 0 638 303 B1 | 11/1997 |
| EP | 0 850 626 A1 | 7/1998 |
| EP | 0 946 211 B1 | 1/2003 |
| EP | 1779828 A1 * | 5/2007 |
| GB | 2 284 767 A | 6/1995 |
| JP | 2004/279159 A | 10/1992 |
| JP | 09-117473 A | 5/1997 |
| WO | WO 97/28773 A1 | 8/1997 |
| WO | WO 98/55065 A1 | 12/1998 |
| WO | WO 00/40193 A1 | 7/2000 |
| WO | WO 01/60300 A1 | 8/2001 |
| WO | WO 01/60300 A1 * | 8/2001 |
| WO | WO 02/02041 A1 | 1/2002 |

* cited by examiner

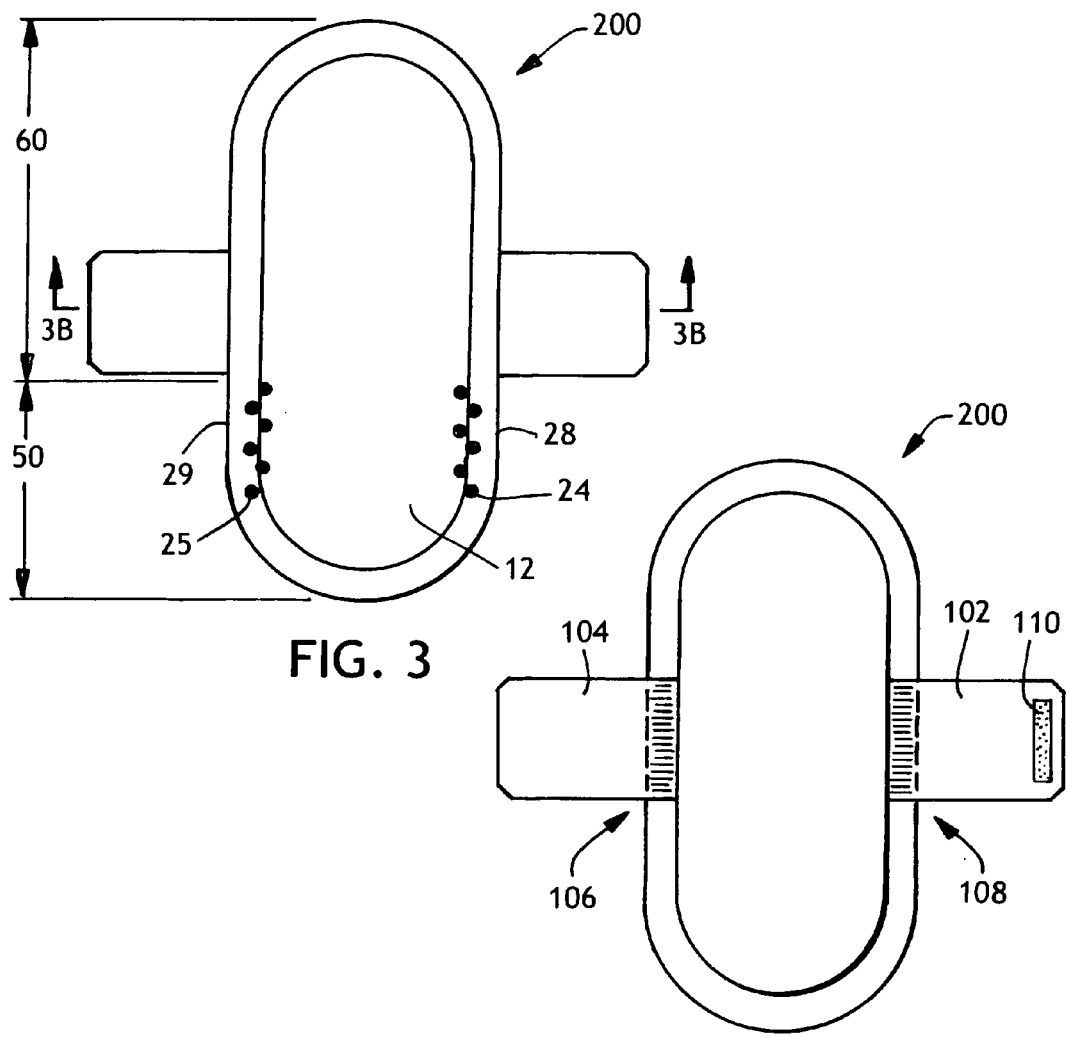
FIG. 3
FIG. 3A
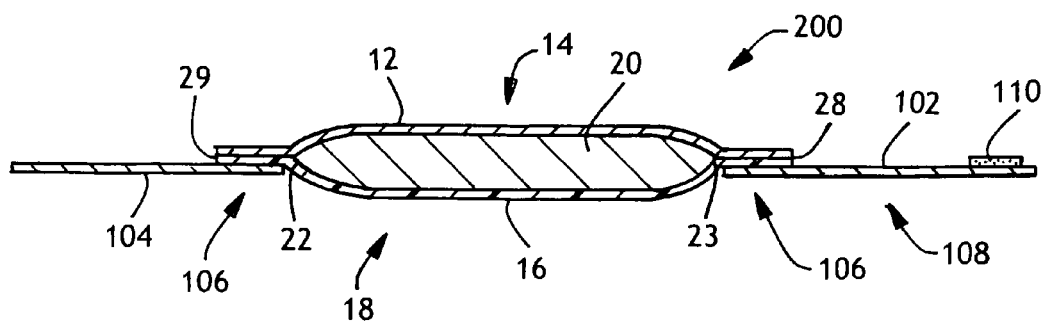
FIG. 3B

BODY-ADHERING PERSONAL CARE PRODUCT

FIELD OF THE INVENTION

The present invention generally relates to an absorbent personal care article having an adhesive on a portion of the body facing layer.

BACKGROUND OF THE INVENTION

Disposable absorbent articles for the absorption and containment of urine, menses and other body exudates are generally known in the art. Generally, these articles are referred to as absorbent personal care articles and have taken various forms including, diapers for infants and children, training pants for children, sanitary napkins, pantiliners, incontinence pads, incontinence garments and the like, for teenagers and adults. Of these absorbent personal care articles, sanitary napkins, incontinence pads and pantiliners are articles which are not garment-like in form, meaning that they do not rely on the body structure of the user to stay in place during use. For example, diapers use the hips and waist of the user to hold the diaper in place during use. As a result, sanitary napkins, pantiliners and incontinence pads are less noticeable and more discrete than diapers and incontinence garments.

Instead, sanitary napkins, pantiliners, and incontinence pads use an undergarment attaching device to hold the article in place during use. Conventional means of holding these absorbent personal care articles in place include, for example, garment attachment adhesives, which are generally pressure sensitive adhesives, attachment panels, which are sometimes referred to as wings or flaps, extending from the longitudinal side edges of the absorbent article which wrap around the undergarment of the user, a body adhesive, which secures the absorbent personal care article directly to the body of a user. In addition, combinations of the attachment devices have also been used.

In selecting an attachment device, several considerations must be considered and balanced. The attachment device must hold the absorbent personal care article in place, providing adequate protection, the attachment device must be comfortable, and the attachment device must be convenient and easy to use. Currently, the most common attachment device is a garment adhesive. While absorbent personal care articles with the garment adhesive attachment device have performed well, remaining in place and providing the user with ease of placement and removal, these absorbent personal care articles have suffered from certain drawbacks. For example, the inner crotch surface of the undergarment to which the absorbent personal care articles are adhered is constantly being distorted, twisted and stretched due to the movements of the wearer. As a result, frequently the garment adhesive detaches with the undesirable result of the sanitary napkin, pantiliner or incontinence pad moving out of position. In an extreme case, detachment of the adhesive may also result in the adhesive folding over on itself and then becoming unavailable for reattachment to the undergarment of the user.

In the case of sanitary napkins, some sanitary napkins have been provided with attachment panels which, in use, are generally folded around the crotch portion of the undergarment and affixed to the outer crotch portion. Although such attachment panels have been partially successful in protecting certain regions of the wearer's undergarment, such sanitary napkins are still subject to the forces which cause the sanitary napkin to be distorted, twisted or stretched.

It has also been suggested in the art to use body adhesives on the body facing surface of a sanitary napkin to secure the sanitary napkin to the wearer's body. This provides a sanitary napkin having intimate contact with the wearer without subjecting the sanitary napkin to the twisting and bunching forces normally exerted on a sanitary napkin secured to the undergarment. However, the proper placement of such a sanitary napkin for maximum absorbent efficiency and comfort may be difficult for users. In addition, having an adhesive on the body-facing surface of the sanitary napkin makes it difficult for a user to perform normal bodily function of removing waste from the body, since the sanitary napkin would have to be removed from the body of the user to perform this bodily function. Often, removing the sanitary napkin from the body of the user will result in the adhesive losing its ability to adhere to the user's body, or the sanitary napkin folding over on itself, causing the adhesive to attach to itself. In either situation, the sanitary napkin will lose its ability to be reattached to the user.

There is a need in the art for an absorbent personal care article, in the form of a sanitary napkin, incontinence pad or pantiliner, which can be effectively held into place against a user's body, providing an effective means to hold the absorbent personal care article in place, thereby providing adequate protection to the user, providing comfort to the user and providing an attachment device which is convenient and easy to use.

SUMMARY OF THE INVENTION

The present invention provides an absorbent article having longitudinal direction, a lateral direction, a second portion and a first portion. This absorbent article has a topsheet which has a first major surface that forms a body-facing surface. In addition, the absorbent article has a backsheet which has a second major surface disposed distally from the first major surface. The second major surface of the backsheet forms a garment-facing surface of the absorbent article. On the second portion of the top sheet on the first major surface, a body adhesive is applied. In the first portion of the absorbent article, a garment-attachment device for attaching the absorbent article to an undergarment of a user is present. The body adhesive applied to the topsheet serves to attach and hold the absorbent article to the body of a user, thereby assisting in preventing the absorbent article from twisting or bunching during normal use and the garment attachment device present on the first portion of the absorbent personal care article serves to hold the absorbent article in contact with the panty of the user.

In the present invention, an absorbent core may be positioned between the topsheet and the backsheet to increase the absorbency of the absorbent article. This absorbent core may be prepared from any conventional absorbent material known to those skilled in the art.

In another embodiment of the present invention, the second portion of the absorbent article is about 10% to about 50% of the longitudinal direction of the absorbent article and the first portion is about 50% to about 90% of the longitudinal direction of the absorbent article. In a further embodiment of the present invention, the second portion of the absorbent article is about ⅓ of the longitudinal direction of the absorbent article and the first portion is about ⅔ of the longitudinal direction of the absorbent article.

In a further embodiment of the present invention, the garment attachment device is an adhesive applied to the second major surface, a mechanical attachment system applied to the second major surface, attachment panels extending from one or both of the longitudinal side edges, attachment panels attached to the second major surface, or a combination thereof.

In another embodiment of the present invention, provided is an absorbent article having longitudinal direction, a lateral direction, a second portion and a first portion. This absorbent article has a topsheet which has a first major surface that forms a body-facing surface. In addition, the absorbent article has a backsheet which has a second major surface disposed distally from the first major surface. The second major surface of the backsheet forms a garment-facing surface of the absorbent article. On the second portion of the topsheet on the first major surface, a body adhesive is applied. In the first portion of the absorbent article, a garment-attachment device for attaching the absorbent article to an undergarment of a user is present. An absorbent core is positioned between the backsheet and the topsheet in the first portion of the absorbent article and the second portion has the backsheet and the top sheet layer. The absorbent core is optionally present in the second portion of the absorbent article.

In a further embodiment of the present invention, the first portion of the absorbent article is divided into a first section and a second section. The second section is proximate to the second portion, each of the first sections and the second sections have a length in the longitudinal direction and the length of the second section being equal to or greater than the length of the first section. In this embodiment, the absorbent article is tri-folded such that the first section is folded over onto the second section and the topsheet of the first section and the topsheet of the second section are in a direct or indirect face to face relationship to one another exposing the backsheet of the first section. The second portion is folded onto the backsheet of the first section such that the body adhesive present on the second portion is in contact with the backsheet of the first section.

In an additional embodiment of the present invention, the first portion of the absorbent article is divided into a first section and a second section, wherein the second section is proximate to the second portion. Each of the first section and the second section have a length in the longitudinal direction, wherein the length of the second section being equal to or greater than the length of the first section. The absorbent article is tri-folded such that the body adhesive present on the second portion is covered with a release liner and the release liner is in a direct or indirect face to face relationship with the topsheet of the second section, thereby exposing the backsheet of the second portion. The first section is then folded onto the backsheet of the second portion such that the backsheet of the second portion is in direct or indirect contact with the topsheet of the first section.

In another embodiment of the present invention, provided is an absorbent article having longitudinal direction, a lateral direction, a first end portion, a second end portion and an intermediate portion, the intermediate portion joining the first end portion to the second end portion. In this embodiment of the present invention, the absorbent article has a topsheet having a first major surface which forms a body-facing surface of the absorbent article. In addition, the absorbent article has a backsheet having a second major surface disposed distally from said first major surface which forms a garment-facing surface of the absorbent article. On the first end portion and the second end portion of the topsheet on the first major surface, a body adhesive is applied. In the intermediate portion of the absorbent article, a garment attachment device for attaching the absorbent article to an undergarment of a user of the absorbent article is present. In this further aspect of this embodiment of the present invention, the intermediate portion of the topsheet of the absorbent article on the body-facing surface is substantially free of any body adhesive.

In yet another embodiment of the present invention, provided is a method of providing a consumer with a choice of how to apply an absorbent article for use. The method includes providing an absorbent article of the present invention having both a garment attachment mechanism and a body adhesive. In the method instructions are also provided to the consumer on how to apply the absorbent article with the body adhesive, and the garment attachment mechanism or a combination of the body adhesive and garment attachment mechanism.

BRIEF DESCRIPTION OF THE DRAWINGS

FIG. 3 shows a body-side view of another exemplary absorbent article of the present invention.

FIG. 3A shows a garment-side view of the exemplary absorbent article of the present invention shown in FIG. 3.

FIG. 3B shows a cross-section of the exemplary absorbent article of the present invention shown in FIG. 3, taken at line 3B-3B.

DEFINITIONS

Figure 1:
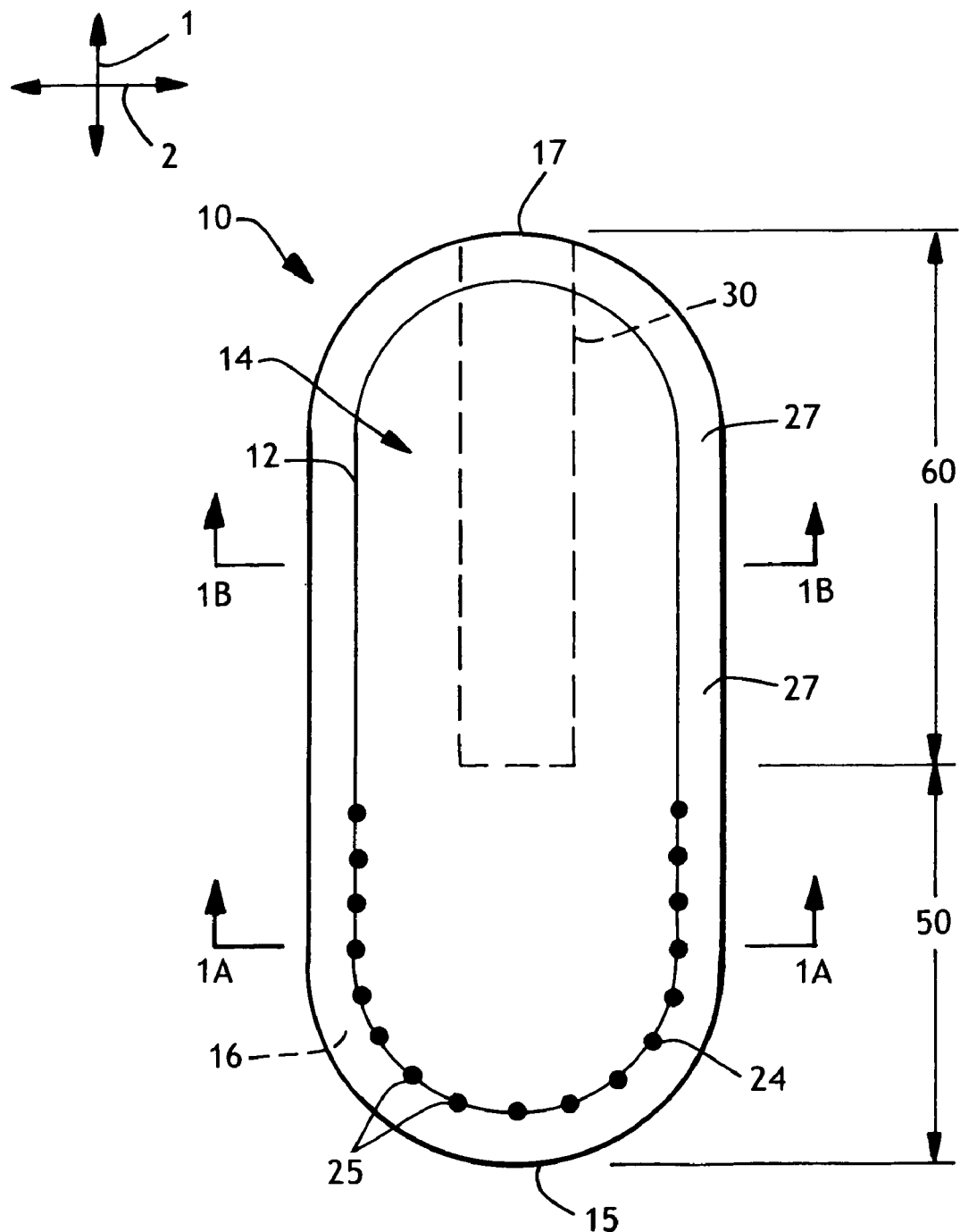
FIG. 1 shows a top or body-side view of an exemplary absorbent article of the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "personal care product" or "personal care article" as used herein refers to any article used to control bodily fluids, and includes "absorbent articles," which refers to any article configured to absorb and retain bodily exudates, including urine, bowel movements, blood and menses, and includes such a product in a packaged and unpackaged configuration. As such, personal care products, as used herein, includes without limitation, diapers, child toilet training pants, adult incontinence garments, male incontinence products, tampons, vaginal suppositories, pantiliners, pads, sanitary napkins, tissues, wipes, etc. Examples of commercially available personal care products include, without limitation, Poise® adult care products, including pantiliners and pads, and Kotex® feminine care products, including pads, tampons and liners, Depend® undergarments, underwear and guards, all available from Kimberly-Clark Corporation, Neenah, Wis.

As used herein, the term "absorbent pad" is intended to include absorbent personal care articles witch are held in place on an undergarment of a user by using an attachment device. Absorbent pads include, for example, sanitary napkins, absorbent incontinence products and pantiliners. Commercially available examples of these products include Poise® adult care products, including pantiliners and pads, and Kotex® feminine care products, including sanitary napkins, and pantiliners, Depend® Guards for Men and Boost liners, all available from Kimberly-Clark Corporation, Neenah, Wis.

As used herein, the term "extensible" refers to articles that can increase in at least one of their dimensions in the x-y plane. The x-y plane is a plane generally parallel to the faces of the article. The term extensible includes articles that are stretchable and elastically stretchable (defined below). In the case of a sanitary napkin comprising an absorbent core, for example, the article and the absorbent core are desirably extensible both in length and width. The absorbent article, however, may only be extensible in one of these directions. Preferably, the article is extensible at least in the longitudinal direction. Examples of extensible materials and articles, and their methods of preparation, are disclosed in U.S. Pat. No. 5,611,790, issued Mar. 18, 1997 to Osborn, Ill. et al., herein incorporated by reference in its entirety.

As used herein, the phrase "substantially free" is intended to mean that small amounts of the substance may be present, but for the most part the substance in not present. For example, trace amounts of the substance may be present or an amount of the substance that will not make the portion of the absorbent article function in the same manner as a portion of the absorbent article containing the substance.

DETAILED DESCRIPTION OF THE INVENTION

The absorbent articles of the present invention have combinations of a body adhesive applied to a portion of the body facing surface and a garment attachment device. This combination of the body adhesive and garment attachment device allows the absorbent article to adhere to the skin of a user, providing an effective means to hold the absorbent personal care article in place during use, providing adequate protection and comfort to a user, while providing an attachment device which is convenient and easy to use. To gain a better understanding of the present invention, attention is directed to the Figures.

Figure 1A:
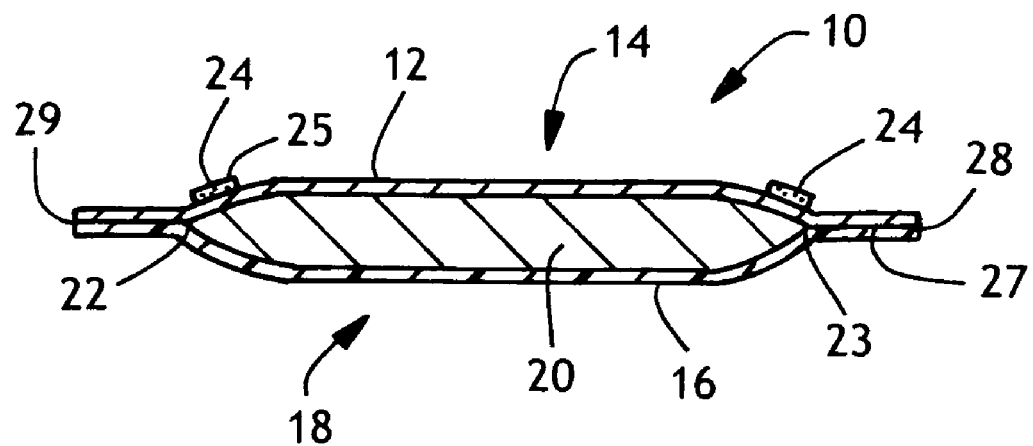
FIG. 1A shows a cross-section of the second portion of an exemplary absorbent article of the present invention shown in FIG. 1, taken at line 1A-1A.
Figure 1B:
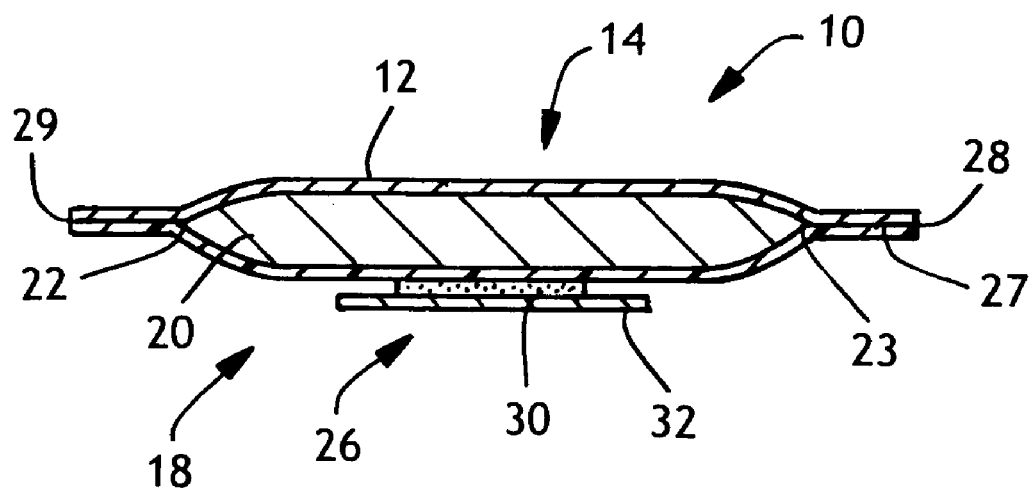
FIG. 1B shows a cross-section of the first portion of an exemplary absorbent article of the present invention shown in FIG. 1, taken at line 1B-1B.

Referring to FIGS. 1, 1A and 1B, shown is an absorbent article 10 having a topsheet 12, the topsheet having a first major surface 14 which is adapted to be positioned adjacent a user's body, thereby forming a body-facing surface of the absorbent article. The absorbent article also has a backsheet 16, the backsheet having a second major surface 18 which is adapted to form a garment-facing surface of the absorbent article. The second major surface 18 is positioned distally from the first major surface 14, such that the first and second major surfaces are facing directions opposite one another. In addition, the absorbent article has a longitudinal direction 1 and a lateral direction 2. Optionally, the absorbent article 10 may have an absorbent core 20 positioned between the topsheet 12 and the backsheet 16. Generally, the topsheet 12 and backsheet 16 are joined to one another along the periphery 27 of the absorbent article as shown in FIGS. 1, 1A and 1B, when an absorbent core is present, or can be joined to one another at the surfaces which are opposite the first and second major surfaces, when an absorbent core is not present (not shown).

In the present invention, the absorbent article 10 has a first portion 60 and a second portion 50. Generally, the second portion 50 during use will be positioned towards the rear of the user and the first portion 60 will be positioned towards the front of a user during use. However, in using the present invention, it is not necessary that the second portion 50 be placed towards the rear of a user and the first portion 60 does not have to be positioned near the front of a user during use. It is generally desirable that the second portion 50 of the absorbent article 10 is positioned near the back of the user during use and the first portion 60 is positioned towards the front of a user, since the body adhesive can provide beneficial effects, such as improved leakage protection, for reasons that will be explained later.

A body adhesive 24 is applied to the first major surface 14 of the topsheet 12 in the second portion 50 of the first major surface 14. The body adhesive 24 allows the absorbent article to be adhered to the body of a user of the absorbent article. In one embodiment of the present invention, the body adhesive 24 is essentially confined to the second portion 50 on the first major surface 14 of the absorbent article 10. By the phrase "essentially confined to the second portion 50 of the first major surface 14" it is intended that the majority of the body adhesive located on the first major surface is located on the second portion of the first major surface of the absorbent article. Stated another way, the body adhesive 24 may be present on the first major surface of the first portion, but the majority of the body adhesive is present on the second portion of the first major surface of the absorbent article. In this embodiment of the present invention, ideally the body adhesive is not present on the first portion 60 of the first major surface of the absorbent article 10, or if it is present, it is only present in a small amount on the first major surface compared to the amounts of the body adhesive present on the second portion on the first major surface. In one particular embodiment of the present invention, the first portion of the first major surface is substantially free of the body adhesive. Desirably, the first portion 60 is devoid of any body adhesive. The body adhesive 24 may be applied in a discontinuous pattern or a continuous pattern on the surface of the first major surface 14. In another embodiment of the present invention, which is described later herein, the body adhesive may be present on both the second end portion and a select section of the first end portion of the absorbent article.

A garment-attachment device is used to attach the first portion 60 of the absorbent article to the undergarment of a user. The garment-attachment device is located on the first portion 60 of the absorbent article 10. Optionally, a garment-attachment device may be present on the second portion 50 of the absorbent article. Generally, in the present invention, suitable garment-attachment devices include, for example, an adhesive applied to the second major surface, a mechanical attachment system applied to the second major surface, attachment panels extending from each longitudinal side edges, attachment panels attached to the second major surface, or a combination thereof. Each of these garment attachment devices will be described in more detail herein below.

The topsheet 12 is sometimes referred to as the bodyside liner or cover of the absorbent article. In one embodiment of the present invention, the topsheet 12 is generally liquid permeable. In addition, the topsheet may be formed from one or more materials. The topsheet 12 must be able to manage different body excretions, depending on the type of product. In feminine care products, often the body-side liner or body contacting layer must be able to handle menses and urine. In the present invention, the body-side liner or topsheet 12 may include a layer constructed of any operative material, and may be a composite material. For example, the topsheet 12 may be prepared from materials such as a woven fabric, a nonwoven fabric, a polymer film, a film-nonwoven fabric laminate or the like, as well as combinations thereof. Examples of a nonwoven fabric useable in the topsheet 12 include, for example, an airlaid nonwoven web, spunbond nonwoven web, meltblown nonwoven web, a bonded carded web, hydroentangled nonwoven web, spunlace web or the like, as well as combinations thereof. Other examples of suitable materials for constructing the topsheet 12 can include rayon, bonded carded webs of polyester, polypropylene, polyethylene, nylon, heat-bondable fibers finely perforated film webs, net-like materials, and the like, as well as combinations thereof. These webs can be prepared from polymeric materials such as, for example, polyolefins, such as polypropylene and polyethylene and copolymers thereof, polyesters in general, including aliphatic esters such as polylactic acid, nylon or any other heat bondable materials.

Other examples of suitable materials for the topsheet 12 are composite materials of a polymer and a nonwoven fabric material. The composite materials are typically in the form of integral sheets generally formed by the extrusion of a polymer onto a nonwoven web, such as a spunbond material. In a desired arrangement, the topsheet 12 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the body side liner or body contacting layer. The apertures or other openings can help increase the rate at which bodily liquids can move through the thickness of the body-side liner or body contacting layer and penetrate into the other components of the article (e.g. into the absorbent core 20). The selected arrangement of liquid-permeability is desirably present at least on an operative portion of the topsheet 12, which is appointed for placement on the body-side of the absorbent article. The topsheet 12 can provide comfort and conformability, and can function to direct bodily exudates away from the body and toward the absorbent core 20, if present. The topsheet 12 can be configured to retain little or no liquid in its structure, and can be configured to provide a relatively comfortable and non-irritating surface next to the body-tissues of a wearer. Alternatively, in the case of pant-iliners without an absorbent core, the topsheet 12 can be configured to retain liquids in its structure. Other topsheet materials which are extensible may be used in the present invention. Examples of extensible topsheet materials are described in U.S. Pat. No. 5,611,790, issued Mar. 18, 1997 to Osborn, Ill. et al., herein incorporated by reference in its entirety.

The backsheet 16, which is sometimes referred to as a baffle, may include a layer constructed of any operative material, and may or may not have a selected level of liquid-permeability or liquid-impermeability, as desired. In a particular configuration, the backsheet 16 may be configured to provide an operatively liquid-impermeable structure. The backsheet 16 may, for example, include a polymeric film, a woven fabric, a nonwoven fabric or the like, as well as combinations or composites thereof. For example, the backsheet 16 may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Suitably, the backsheet 16 can operatively permit a sufficient passage of air and moisture vapor out of the article, particularly out of an absorbent material (e.g. storage or absorbent core 20) while blocking the passage of bodily liquids. An example of a suitable baffle material can include a breathable, microporous film, such as those described in, for example, U.S. Pat. No. 6,045,900 to Haffner et al., the entire disclosure of which is incorporated herein by reference and made a part hereof. Other backsheet materials which are extensible may be used in the present invention. Examples of extensible backsheet materials are described in U.S. Pat. No. 5,611,790, issued Mar. 18, 1997 to Osborn, Ill. et al., herein incorporated by reference in its entirety.

Bicomponent films or other multi-component films can also be used, as well as woven and/or nonwoven fabrics which have been treated to render them operatively liquid-impermeable. Another suitable backsheet material can include a closed cell polyolefin foam. For example, a closed cell polyethylene foam may be employed.

The absorbent core 20, when present, is designed to absorb body exudates, including menstrual fluid, blood, urine, and other body fluids. The absorbent core 20 may contain one or more layers of absorbent materials. The layers can contain similar materials or different materials. Suitable materials for the absorbent core 20 include, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form, and has good absorbency.

The absorbent core 20 can also be formed from a composite comprised of a hydrophilic material which may be formed from various natural or synthetic fibers, wood pulp fibers, regenerated cellulose or cotton fibers, or a blend of pulp and other fibers. A desired material is an airlaid material. Other absorbent core materials which are extensible may be used in the present invention. Examples of extensible absorbent core materials are described in U.S. Pat. No. 5,611,790, issued Mar. 18, 1997 to Osborn, Ill. et al., herein incorporated by reference in its entirety.

In one embodiment, the absorbent core 20 also includes a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, and Stockhausen, Incorporated, among others, and are a partially neutralized salt of cross-linked copolymer of polyacrylic acid and polyvinyl alcohol having an absorbency underload value of above 25 grams of absorbed liquid per gram of absorbent material (g/g). Other types of superabsorbent materials known to those skilled in the art can also be used.

Additional layers or substrates, including for example, the liquid acquisition and distribution layer, also referred to as a surge or transfer layer, and an optional tissue layer may also be incorporated into the absorbent product, for example, between the topsheet 12 and the absorbent core 20. The distribution layer may be shorter than the absorbent core 20 or have the same length as the absorbent core 20. The distribution layer serves to temporarily hold an insulting fluid to allow the absorbent core sufficient time to absorb the fluid, especially when a superabsorbent material is present. In one embodiment, the absorbent core, transfer layer and other components, such as tissue layers, are free floating (unattached) between the outer cover and the body-side liner, which are secured along only the peripheral edges thereof. Alternatively, the absorbent core, transfer layer and other components are attached to one or both of the outercover and topsheet and/or to each other.

As is described above, the components of the absorbent article may be selected such that the components are extensible, which in turn will make the absorbent article extensible. By having an extensible absorbent article, the absorbent article may be more comfortable to wear for the user since there are competing forces applied to the absorbent article during use. That is, the absorbent article is typically subjected to a twisting motion while a user is walking. By having the absorbent article being extensible, the absorbent article will be able to absorb most of the twisting motion rather than the body adhesive used to apply the absorbent article to the body of a user.

The topsheet 12 and the backsheet 16 may be peripherally sealed together to enclose the optional absorbent core 20 to form the absorbent article 10, as is shown in FIGS. 1, 1A and 1B. When a peripheral seal 27 is in use, the absorbent 20 is positioned between the topsheet 12 and the backsheet 16. Referring to FIGS. 1, 1A and 1B, the topsheet 12 and the backsheet 16 can have a length and a width dimension greater than the length and width of the absorbent 20, extending beyond the absorbent sides 22 and 23 encasing the absorbent 20 and defining longitudinal side edges 28 and 29 of the absorbent article 10. The topsheet 12 and the backsheet 16 may be sealed together using any suitable means that will not leave a hard, uncomfortable residue that may be annoying to the wearer. As used herein, the term "sealed" encompasses configurations whereby the topsheet 12 is directly joined to the backsheet 16 and configurations whereby the topsheet 12 is indirectly joined to the backsheet 16 by affixing the topsheet 12 to an intermediate member (not shown), which are in turn affixed to the backsheet 16. Alternatively, the topsheet 12 can be wrapped around both the absorbent core 20 and the backsheet 16 to form a wrapped pad. The topsheet 12 and backsheet 16, and other components of the absorbent product, can be joined, for example, with adhesive bonds, sonic bonds, thermal bonds, pinning, stitching or any other attachment technique known in the art, as well as combinations thereof.

The body adhesive 24 is positioned on the second portion 50 of the first major surface 14 to contact the wearer and support the absorbent article 10 during use. The body adhesive 24 can overlie from about 5 percent to about 95 percent of the second portion 50 of the first major surface 14. Generally, the adhesive 24 overlies from about 5 percent to about 75 percent of the second portion of the first major surface 14. In most applications, the adhesive 24 overlies from about 5 percent to about 35 percent of the second portion 50 of the first major surface 14, more preferably, from about 5 percent to about 20 percent of the second portion 50 of the first major surface 14.

Generally, any pressure sensitive adhesive known to those skilled in the art may be used, provided that the pressure sensitive adhesive is not a known irritant to human skin or that the adhesive is so aggressive that it causes pain to the user when the absorbent article is removed from the skin. Desirably, the adhesive should be selected such that the adhesive does not leave a substantial amount of an adhesive residue on the surface of the skin of the user, when the absorbent article 10 is removed by the user after use. Particularly suitable pressure sensitive adhesive materials are disclosed in the commonly assigned U.S. Pat. No. 6,213,993 to Zacharias et al., U.S. Pat. No. 6,620,143 to Zacharias et al., the entire disclosure of each is incorporated herein by reference and made a part hereof. Other suitable adhesives are disclosed in U.S. Pat. No. 5,618,281 to Batrabet et al., the entire disclosure of which is incorporated herein by reference and made a part hereof.

The body adhesive 24 may be positioned on the second portion of the topsheet 12 in an open or a closed pattern. By "open" is meant that the adhesive can have an intermittent or continuous pattern which does not substantially cover the transverse ends 15 of the second portion 50 of the absorbent article 10. "Closed" means the adhesive would encircle the absorbent core 20 at the transverse end 15 of the second portion 50. Preferably, the pattern of the adhesive 22 substantially corresponds to the configuration of the absorbent core 20 in the second portion 50. As shown in FIG. 1, the body adhesive 24 is applied in a closed pattern, since the transverse end 15 of the absorbent core 20 is encircled at the end. An "open" pattern of the adhesive is shown in FIG. 3. In the present invention, the closed pattern can be advantageous since the body adhesive may form a seal with the body of the user which will assist in preventing leaks from the absorbent article. This advantage can be obtained when the second portion of the absorbent article is placed near the rear of a user during use. The body adhesive may form a dam, which will prevent leaks from the rear portion of the absorbent article.

Figures 2, 2A:
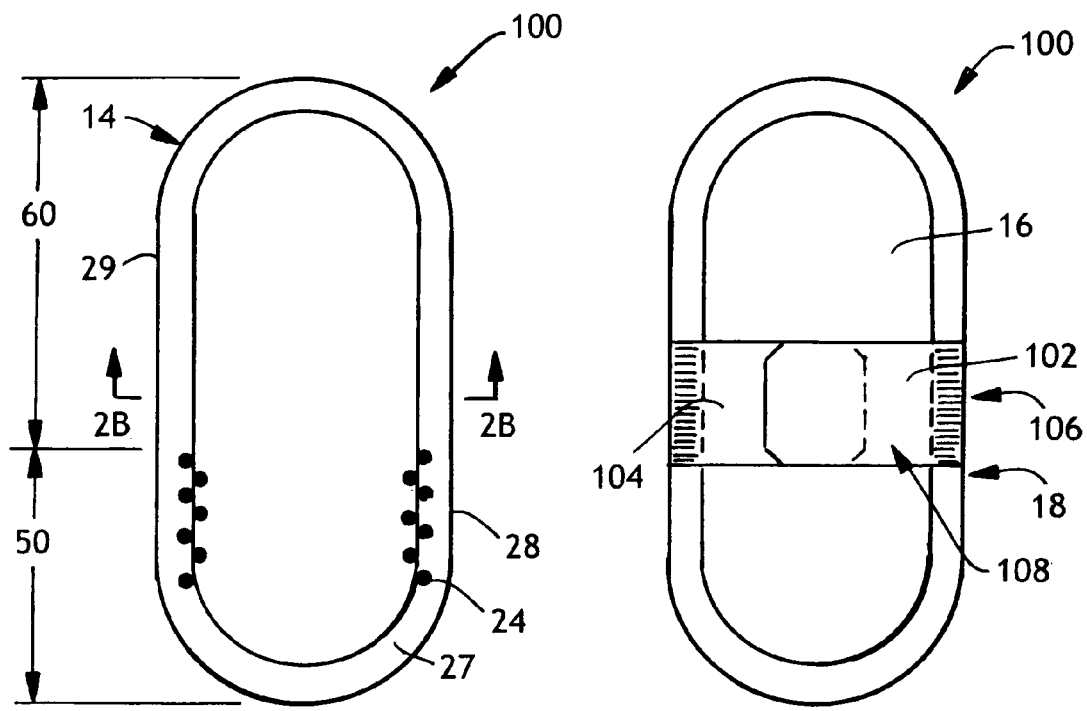
FIG. 2 shows a top or body-side view of another exemplary absorbent article of the present invention.
FIG. 2A shows a garment-side view of the exemplary absorbent article of the present invention shown in FIG. 2.

In one embodiment of the present invention, as is shown in FIGS. 1 and 1A, the body adhesive 24 may be placed along the outer portions of the absorbent core 20 near the periphery seal 27. In another alternative embodiment of the present invention, as is shown in FIG. 2, the body adhesive 24 is placed along the outer portions of the absorbent core 20 near the periphery seal 27 and along the periphery seal 27 adjacent the absorbent core 20. In yet another embodiment of the present invention, shown in FIG. 10, the body adhesive 24 is placed along the periphery seal adjacent the absorbent core 20. Alternatively, the body adhesive may be randomly placed on the topsheet 12 of the absorbent article (not shown).

The adhesive may be applied in a pattern of small discrete dots or adhesive members 25 so as to leave numerous areas free from adhesive, as is shown in FIG. 1. The adhesive members 25 can have a surface area of about 0.03 $cm^2$ to about 20 $cm^2$ and preferably about 0.15 $cm^2$ to about 15 $cm^2$. As measured from the first major surface 14 of the topsheet 12, the adhesive members 25 can have a thickness of about 0.01 millimeters to about 2 millimeters. In the present invention, the length of the body adhesive should be at least about 2 inches (5 cm) in the longitudinal direction of the absorbent article 10. In addition, the body adhesive may be placed on the top sheet of the absorbent article in a width in the lateral direction of about 3 mm to about 8 mm. The body adhesive may be applied as discrete beads on the topsheet, or may be applied as a continuous bead of the body adhesive. Alternatively, the adhesive may be applied as a continuous bead, as shown in FIG. 2, or may be applied as a serious of semi-continuous beads, as shown in FIG. 3.

Other suitable adhesive patterns may be selected for applying the body adhesive 24 to the body-facing surface 14 of the absorbent article 10, such that it is consistent with the concentration of body adhesive 24 desired on the second portion 50 of the first surface 16, yet allowing the absorbent article 10 to retain the requisite amount of absorbency. For example, adhesive patterns can be oval, swirls, various linear or non-linear arrays of adhesive longitudinally, and/or transversely oriented and reticulated webs having unobstructed interstices between the adhesive fibers or combinations thereof. As stated above, the adhesive patterns may be open or closed. The weights of adhesives are limited to less than about 1500 $mg/in^2$, and generally less than about 800 $mg/in^2$. The limitations on the weight of the adhesive are important to provide the correct adhesive characteristics for applying directly to the wearer's pudendal region.

Generally, the body adhesive 24 is applied in a pattern which is symmetrical about the longitudinal axis which bisects the absorbent article 10 and divides the absorbent 10 into substantially equal portions. This symmetrical pattern provides the wearer a balanced feel when wearing the absorbent article 10. The symmetrical pattern also reduces the perception of any associated discomfort when the absorbent article 10 is removed from the body. To protect the adhesive, a peel strip or release strip (not shown) may be used to prevent the body adhesive 24 from becoming contaminated and/or prematurely adhering to an unintended surface. Suitable materials for use as a peel strip are well known in the art and are commercially available. Examples of suitable peel strips or release strips include, for example, a silicone coated Kraft paper, film or the like.

The body adhesive 24 can be applied to the second portion 50 of the first surface 14 using any known process including, inkjet printing, screen printing or extruding the body adhesive 24 from one or more nozzles, slot coating and the like.

Absorbent article 10 of the present invention further has a garment attachment device located on at least the first portion 60 of the absorbent article 10. By the phrase "on at least the first portion" it is intended that a garment attachment device is located on the first portion 60 and may be present on the second portion 50. Generally and desirably, the garment attachment device is only present on the first portion 60. Suitable garment attachment devices include an adhesive applied to the second major surface, a mechanical attachment system applied to the second major surface, attachment panels extending from one or both of the longitudinal side edges, attachment panels attached to the second major surface, or a combination thereof. Each one of these garment attachment devices will be described in more detail below.

As is shown in FIGS. 1, 1A and 1B, the garment attachment device 26 is a garment adhesive. Applied to at least a portion of the second major surface 18 of the backsheet 16 is a garment adhesive 30. Garment adhesives are well known in the art and have been widely used in absorbent articles, such as sanitary napkins, incontinence pads and pantiliners. Generally, garment adhesives are pressure sensitive adhesives. Any garment adhesive known to those skilled in the art may be used in the present invention. In various embodiments, the garment adhesive may be configured as a single band of adhesive or as two or more spaced apart strips. Alternatively, the garment attachment adhesive includes a swirl pattern of adhesive which encompasses a major portion of the second major surface 18 of the absorbent article 10.

In one embodiment of the present invention, the garment adhesive is selected such that the modulus of the garment adhesive is similar to that of the body adhesive. If the modulus of the garment adhesive is similar to that of the body adhesive, the competing forces applied to the absorbent article during use may be lessened, thereby making the absorbent article more comfortable for a user to wear. The competing forces are the forces which hold the absorbent article to the undergarment of the user and the forces of the body adhesive used to hold the absorbent article to the user. During use, the absorbent article may be subjected to a twisting force while a user is walking, which may cause the absorbent article to twist during use. If the forces holding the absorbent article to the user are similar to the forces used to hold the absorbent article to the panty of a user, the absorbent article may be less likely to pull away from the skin of a user during use. In one particular embodiment, the same body adhesive used on the second portion of the absorbent article may be used as the garment adhesive.

A release strip 32, also known as a peel strip, is removably secured to the garment adhesive and serves to prevent premature contamination of the adhesive before the absorbent article 10 is secured to the crotch portion of an undergarment. In various embodiments, the garment attachment adhesive is designed to be secured to the inner crotch portion of an undergarment so as to keep the absorbent product in register with the body of the user. The release strip 32 may extend beyond one or both of the ends 15, or 17 of the absorbent article, as shown in FIG. 1. Alternatively, the release strip may be as short as the length of the garment adhesive, or slightly longer than the adhesive or may be only as long as the garment attachment adhesive, but does not extend beyond the ends 15 and 17 of the absorbent article 10.

Figure 2B:
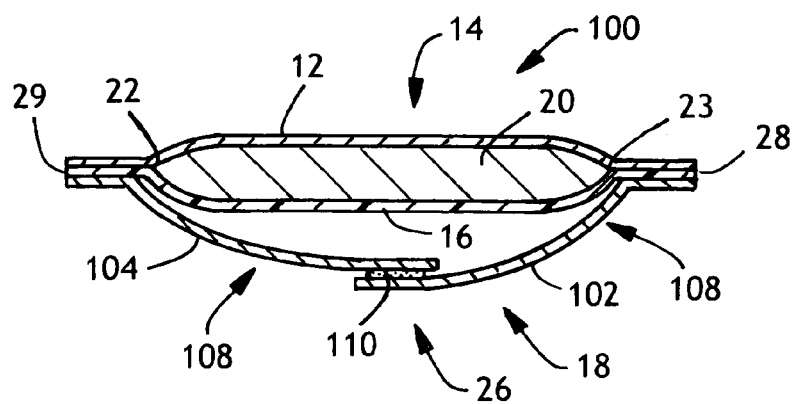
FIG. 2B shows a cross-section of the first portion exemplary absorbent article of the present invention shown in FIG. 2, taken at line 2B-2B.

Another garment attachment device usable in the present invention is shown in FIGS. 2, 2A and 2B, which show an embodiment of an absorbent article 100. The absorbent article 100 is similar to that described above for FIG. 1, except the garment attachment device 26 includes an attachment panel 102, and preferably, a pair of attachment panels 102 and 104 secured to the absorbent article 100. These attachment panels are also referred to as wings or flaps. The attachment panels 102 and 104 secure the absorbent article 100 to the inner crotch portion of the wearer's undergarment for proper placement, supplanting the use of a garment adhesive 30 (seen in FIGS. 1 and 1B). In addition, the panels 102 and 104 can be used in combination with the pressure-sensitive garment adhesive 30. The attachment panels 102 and 104 extend transversely relative to the longitudinal sides 22 and 23 of the absorbent core 20 and are intended to be folded around the crotch portion of the wearer's undergarment and can protect the leg edges from soiling during use. The attachment panels 102 and 104 may be identical or different.

The attachment panel 102 consists generally of a separate sheet of material having a fixed portion 106 and an unaffixed, free portion 108. The fixed portion 106 is secured to the second major surface 18 at a location that generally coincides with or is inward from the longitudinal side edge 28 of the absorbent article 100. The attachment panel 102 can be secured to the second major surface 18 in any manner which results in a sufficiently strong and flexible juncture between the two materials. Accordingly, the choice of materials may dictate the choice of method for affixing the panel 102 to the second major surface 18. Suitable methods utilized can include adhesives, heat bonding, ultrasonics and the like.

The free portion 108 of the panel 102 extends from the fixed portion 106 and is directed generally inward relative to the longitudinal side edge 28 of the absorbent article 100. The free portion 108 of at least one and preferably both attachment panels 102 and 104 are provided with a securement device 110 for securement when the attachment panels 102 and 104 are folded over the respective leg edge of the undergarment crotch portion. Preferably, the attachment panels 102 and 104 are configured to encircle the crotch portion of the wearer's undergarments during use. In this preferred configuration, the attachment device 110 is positioned on the free portion 108 so that at least a portion of the attachment panel 102 and 104 may be secured together under the outer crotch portion of the undergarment. The attachment device 110 can be pressure-sensitive adhesives, cohesives or mechanical fasteners, such as, hook-and-loop materials, snaps, buttons and the like.

Referring to FIGS. 3, 3A and 3B another embodiment of an absorbent article 200 is shown. The absorbent article 200 is similar to that described above for FIGS. 4-6. The attachment panels 102 and 104 are secured to the second major surface 18 at a location that generally coincides with or is inward from the longitudinal side edge 28 and 29. For FIGS. 2, 2A, 2B, 3, 3A and 3B, when referring to a point or location of securement of the fixed portion 106 of the panels 102 and 104 being generally coincident to or inward from the longitudinal side edge 28 or 29 of the absorbent article 100 and 200, it is meant the point of affixation closest to the longitudinal edge 28 or 29. The embodiment illustrated in FIGS. 3, 3A and 3B differs from the embodiments of FIGS. 1, 1A, 1B, 2, 2A and 2B in that the free portion 108 of the attachment panels 102 and 104 extends outward relative to the longitudinal edge 28 or 29. Similarly, the free portion 108 of at least one and preferably both attachment panels 102 and 104 are provided with an attachment device 110 for securement of each attachment panel 102 and 104 when they are folded over the respective leg edge of the undergarment crotch portion. Preferably, the attachment panels 102 and 104 are configured to encircle the crotch portion of the wearer's undergarments during use. In this preferred configuration, the securement device 110 is positioned on the free portion 108 so that at least a portion of the attachment panel 102 and 104 may be secured together under the outer crotch portion of the undergarment. The securement device 110 can be a pressure-sensitive adhesive, cohesives or mechanical fasteners, such as hook-and-loop materials, snaps, buttons and the like.

Figure 4:
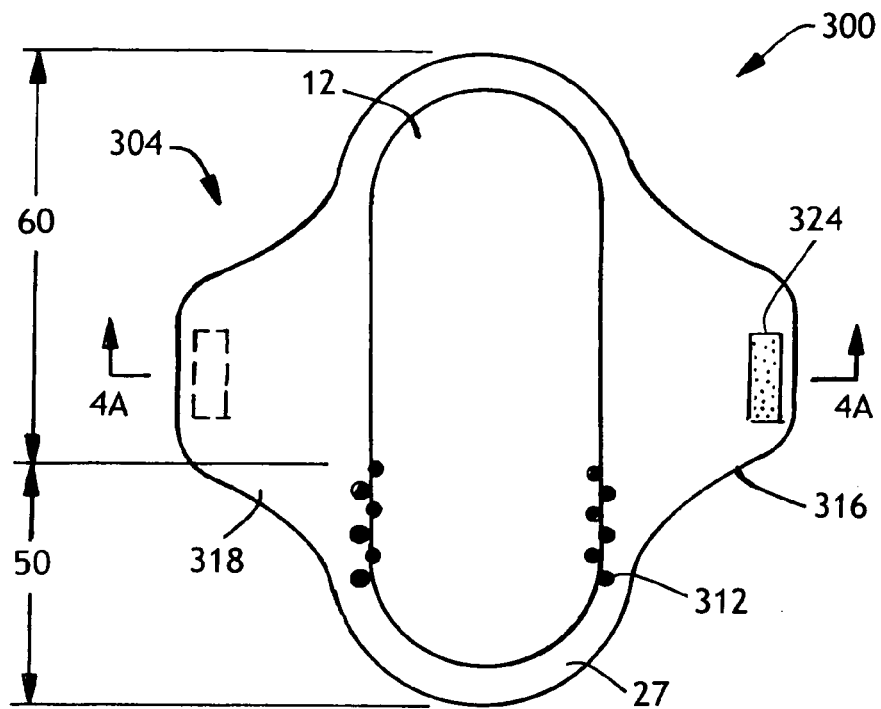
FIG. 4 shows a body-side view of another exemplary absorbent article of the present invention.
Figure 4A:
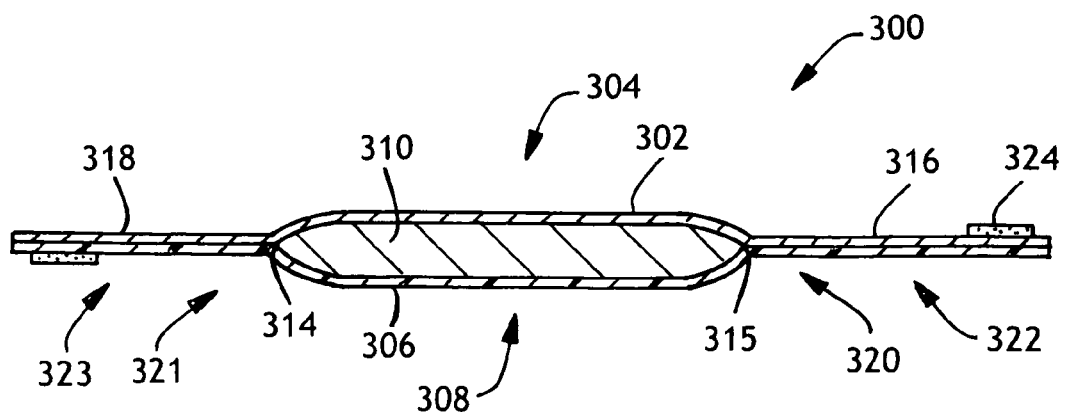
FIG. 4A shows a cross-section view of the exemplary absorbent article of the present invention shown in FIG. 4, taken at 4A-4A.
Figure 4B:
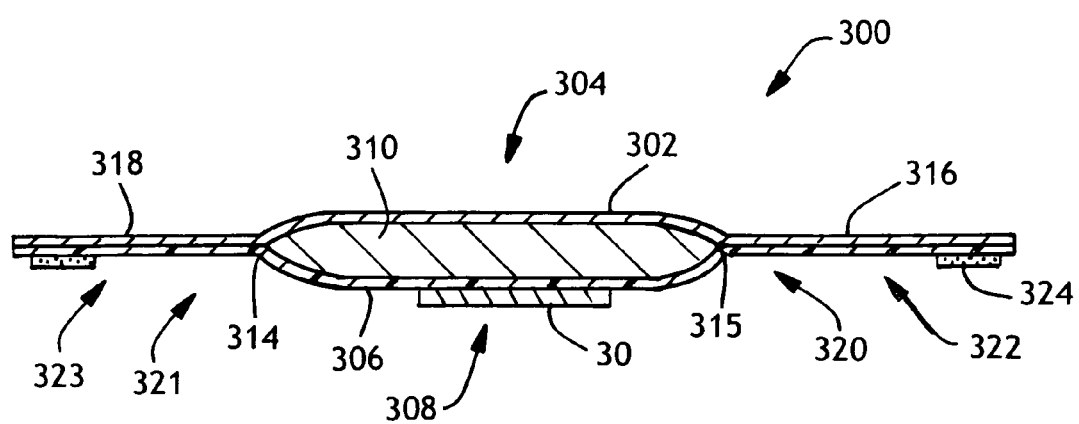
FIG. 4B shows another cross-section of the exemplary absorbent article of the present invention shown in FIG. 4, taken at line 4B-4B.

Referring to FIGS. 4 and 4A, another embodiment of the invention is illustrated. The absorbent article 300 has a topsheet 302 with a first major surface 304, a backsheet 306 with a second major surface 308 and an absorbent core 310 located between the topsheet 302 and the backsheet 306. The topsheet 302, backsheet 306, first and second major surfaces 304 and 308 are similar to that described above for FIGS. 1, 1A, 1B, 2, 2A, 2B, 3, 3A and 3B. The absorbent article 300 includes a body adhesive 312 secured to the first major surface 304 for adhering the absorbent article 300 to the wearer's body during use similar to that described above for FIGS. 1, 1A, 1B, 2, 2A, 2B, 3, 3A and 3B. The topsheet 302 and backsheet 306 extend beyond the longitudinal sides 314 and 315 of the absorbent core 310 to define laterally extending panels 316 and 318. In effect, the topsheet 302 forms one surface of the attachment panels 316 and 318 while the backsheet 306 forms the other surface. In general, the panels 316 and 318 do not require a topsheet 302 to enable them to function properly, but the use of a topsheet 302 is preferred. The panels 316 and 318 permit the absorbent article 300 to be positioned in the crotch area of a wearer's undergarment for proper positioning of the absorbent article 300 against the wearer's body during use.

The panels 316 and 318 are integrally formed by the extension of the cover and the baffle beyond the longitudinal sides 314 and 315 of the absorbent core 310. The panels 316 and 318 have a fixed portion 320 and 321 positioned adjacent to the longitudinal sides 314 and 315 and a free portion 322 and 323 extending from the fixed portions 320 and 321. In forming the panels 316 and 318, the cover 302 and baffle 306 can be secured together by any means commonly used in the art for this purpose, such as adhesive, ultrasonic bonding, heat bonding, crimping, or the like.

The free portion 322 and 323 of panels 316 and 318 are sufficiently flexible to allow each panel 316 and 318 to be positioned around a leg edge of the crotch portion of a wearer's undergarment without appreciably altering the natural path of the leg edge. The precise shape of each panel 316 and 318, as well as the overall shape of the sanitary napkin 300, is not critical to the invention to the extent that it does not interfere with the body adhesive 312 in securing the sanitary napkin 300 to the wearer. Accordingly, depending upon the intended usage of the sanitary napkin 300, the shape of the absorbent article 300 and the panels 316 and 318 can be readily selected by those skilled in the art without undue experimentation. The panels 316 and 318 can be asymmetrically positioned along the longitudinal axis of the sanitary napkin, but preferably, the panels 316 and 318 are symmetrically disposed so that the panels 316 and 318 are mirror images of each other. The attachment panels 316 and 318 include a securement device 324 to assist in maintaining at least one panel 316 and preferably both panels 316 and 318 in position after the panels are wrapped around the crotch portion of the undergarment. The attachment device 324 can include an adhesive, cohesives and mechanical fasteners such as hook-and-loop materials, snaps, buttons and equivalents thereof. The attachment device 324 is preferably positioned on the panels 316 and 318 in a manner that will permit at least one of the panels 316 or 318 to be secured to least a portion of the opposing panel.

Figure 5:
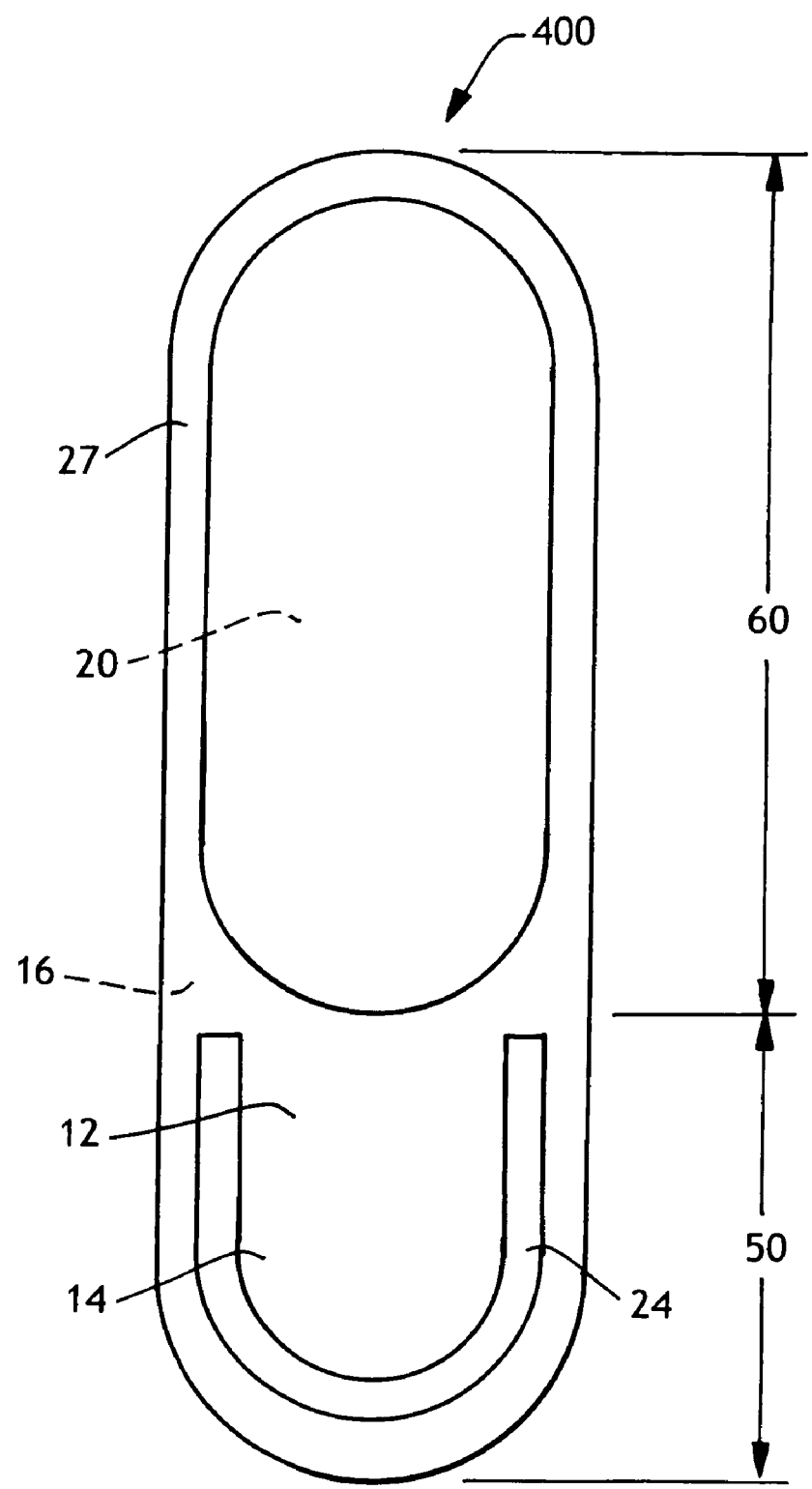
FIG. 5 shows a top view or body-side view of an exemplary absorbent article of the present invention having a second portion extension.

In the embodiments of the present invention shown in FIGS. 1, 1A, 1B, 2, 2A, 2B, 3, 3A, 3B, 4, 4A and 4B, the absorbent core 20 is located in both the first portion and the second portion of the absorbent articles 10, 100, 200 and 300. In another embodiment of the present invention, the second portion of the absorbent article may be devoid of the absorbent core 20. As is shown in FIG. 5, an absorbent article 400 has a second portion 50 and a first portion 60, wherein the second portion 50 is devoid of the absorbent core. As with the other embodiments of the present invention, the body adhesive 24 is located on the topsheet 12 of the second portion 50. The second portion 50 is formed from the top sheet 12 and backsheet 16. The top sheet 12 may be directly or indirectly joined to the backsheet using suitable means to join the materials, including those described above. In the first portion 60 of the absorbent article 400, any of the garment attachment devices (not shown in FIG. 5) described above may be used. In this embodiment of the present invention, the second portion is an extension from the first portion 60 containing the absorbent core 20.

In each embodiment of the present invention, the second portion 50 of the absorbent article is no greater than 50% of the longitudinal length of the absorbent article. Generally, the second portion 50 forms between about 10% and about 50% of the longitudinal length of the absorbent article. In some embodiments, the second portion 50 is between about 20% and about 45% of the longitudinal length of the absorbent article and is typically about 30% and about 40% of the longitudinal length of the absorbent article. In one particular embodiment, the second portion 50 of the absorbent article is approximately ⅓ of the longitudinal length of the absorbent article. Generally, the absorbent articles of the present invention have a longitudinal length of about 5 inches (12.7 cm) to about 20 inches (51 cm). Typically the absorbent articles have a length of about 6 inches (15.2 cm) to about 11 inches (28 cm). The absorbent articles of the present invention may be longer or shorter than these parameters, depending on the use, the size of the user and other factors. For example, in the embodiment of the present invention, which has a second portion extension shown in FIG. 5, the first portion 60 of the absorbent article 400 may have a longitudinal length of about 5 inches (12.7 cm) to about 13 inches (33 cm) and the second portion 50 has a longitudinal length between about 2.5 inches (6.3 cm) to about 6.5 inches (17.5 cm).

Typically, the absorbent core on incontinence pads and sanitary napkins are roughly about 2-3 inches wide (5 cm-8 cm), not including garment attachment flaps or a periphery of only the topsheet and backsheet, when the second portion 50 is an extension. As is shown in FIG. 5, the second portion may be as wide as the absorbent core or may be narrower than the absorbent core.

By providing a second portion 50 of the absorbent articles of the present invention with a body adhesive 24, the body adhesive can be positioned on the body of a user away from the user's pubic hairs, providing a more comfortable absorbent article for the user. Further, by having the body adhesive on the second portion 50 of the absorbent article, the body adhesive will stick to the user's skin, which the adhesive is designed to easily release from, and will not be near the user's pubic hairs which could cause discomfort to the user when the absorbent article is removed form the user's body. In addition, by having the second portion being made from only the topsheet and the backsheet, cost of the absorbent material may be saved and unnecessary use of additional natural resources may also be saved.

Figure 6:
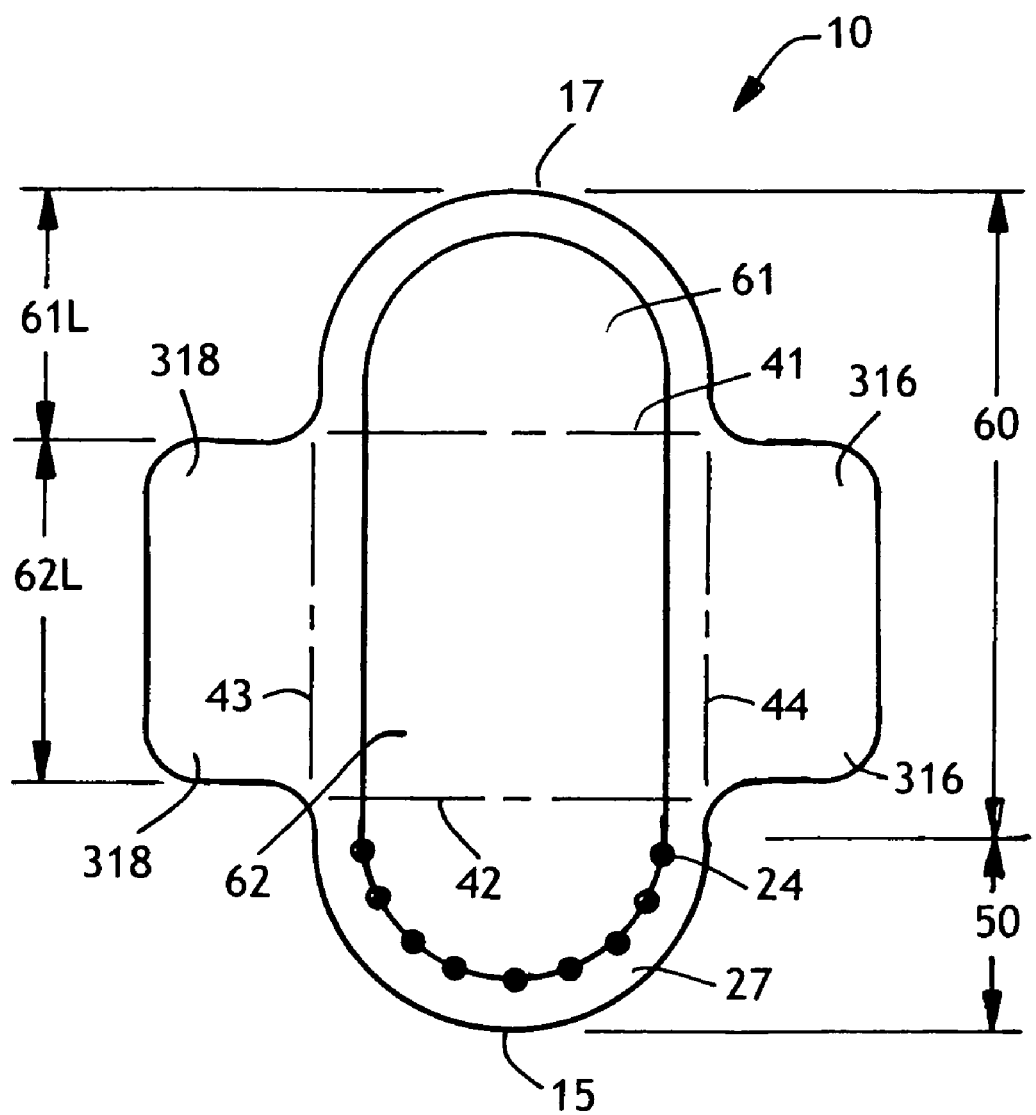
FIG. 6 shows a top view of an exemplary absorbent article of the present invention with tri-folding fold lines configuration.
Figure 7:
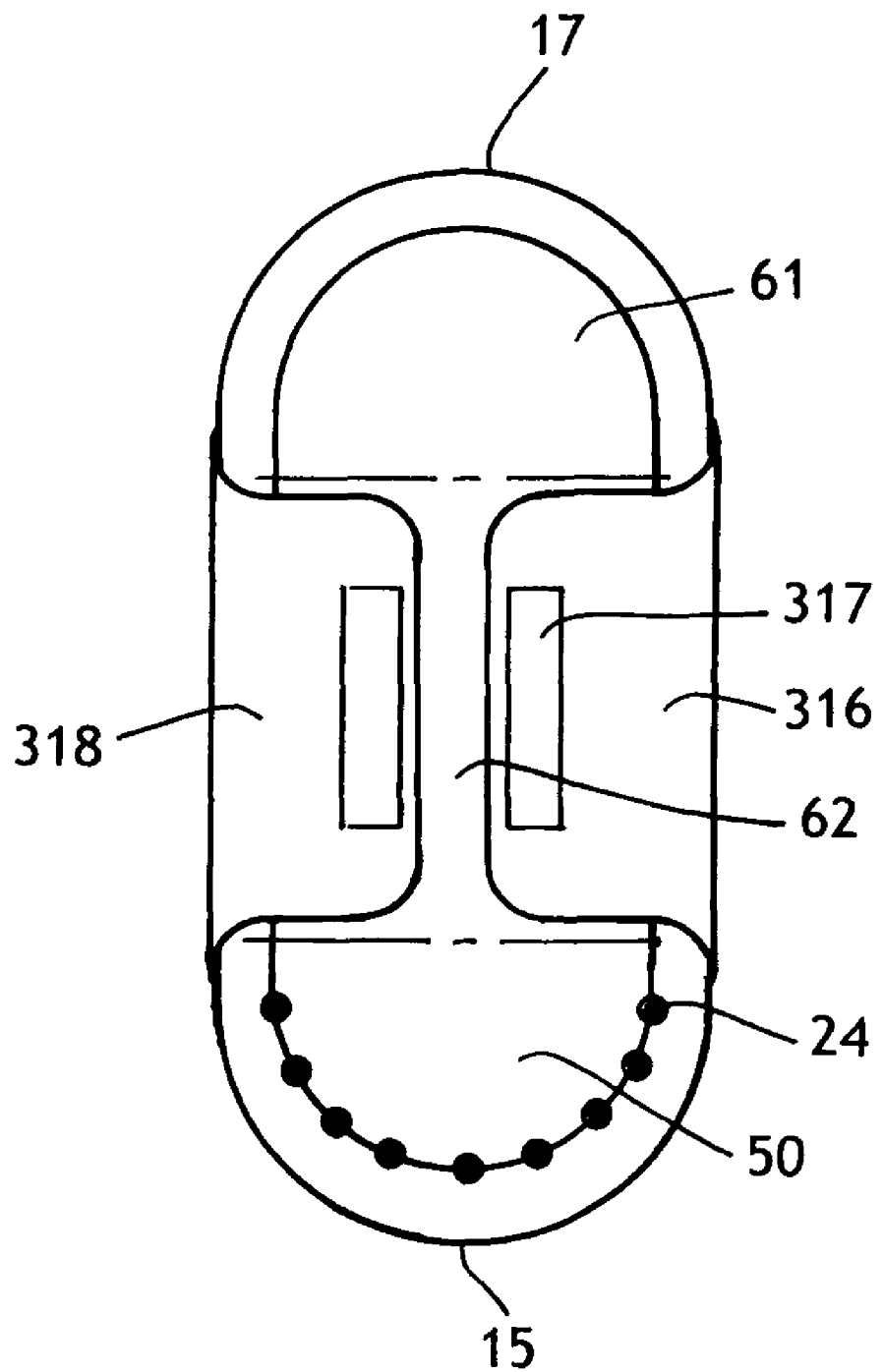
FIG. 7 shows a top view of an exemplary absorbent article of the present invention in a partially tri-folded configuration.

In a further embodiment of the present invention, absorbent articles may be folded. As is shown in FIGS. 6 and 7, the first portion 60 of the absorbent article 10 is divided into a first section 61 and a second section 62. The second section 62 is proximate to the second portion 50, each of the first section 61 and the second section 62 have in the longitudinal direction a length 61L and 62L. The length of the second section 62L is equal to or greater than the length of the first section 61L. In an example of this embodiment, the absorbent article is tri-folded or C-folded such that the first section is folded over onto the second section and the topsheet of the first section and the topsheet of the second section are in a direct or indirect face to face relationship to one another exposing the backsheet of the first section. The second portion is folded onto the backsheet of the first section such that the body adhesive present on the second portion is in contact with the backsheet of the first section.

Figure 8:
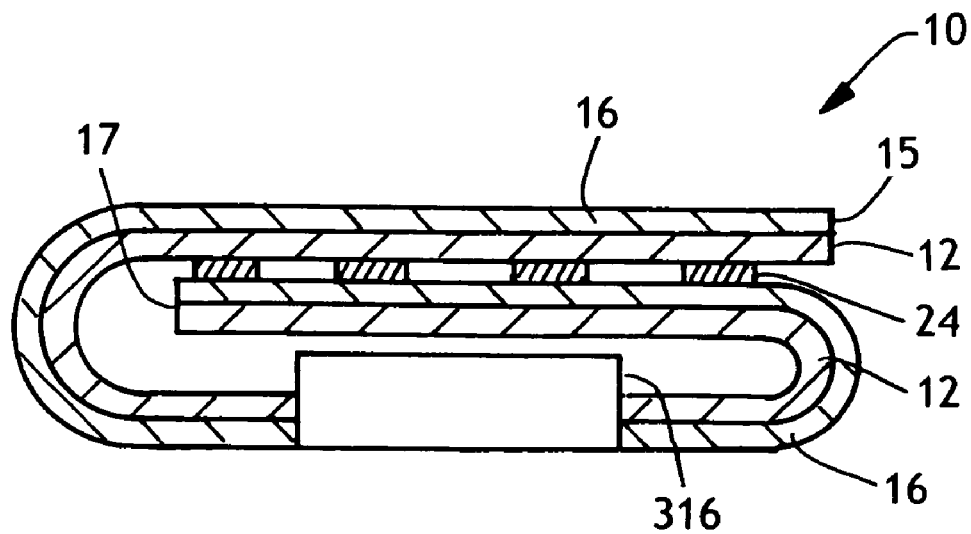
FIG. 8 shows a side view of an exemplary absorbent article of the present invention in a tri-folded configuration.

Referring to FIGS. 6, 7 and 8, the absorbent article 10 has a pair of optional attachment panels 316, 318. The garment attachment panels are shown with a garment adhesive 317, which serves to secure the garment attachment panels to the panty of a user. The attachment panels as shown in FIGS. 6 and 7, when present, are first folded along fold lines 43 and 44 such that the topsheet side of each attachment panel is folded onto the topsheet side of the absorbent article. The fold lines are generally located along the line formed by the longitudinal side edges of the absorbent article. Optionally, a release strip (not shown) may be used to hold the attachment panels in place. The release strip will serve to hold the attachment panels in place during the folding of the absorbent article and will also serve to protect a garment adhesive 317 or other attachment means on the attachment flaps. In an alternative embodiment of the present invention, the attachment panels may be folded under the absorbent article such that the backsheet side of each attachment panel is adjacent the backsheet side of the absorbent article 10.

The two-fold axes 41 and 42 can be located at equal or different distances from the first and second ends, 17 and 15 respectively, of the absorbent article 10, the first end 17 will either be flush with or spaced apart from the fold axes 42, when the first end is folded. In the present invention, the first end 17, which is the longitudinal end of the first section 61, is first folded along fold axes 41 such that the topsheet in the first section 61 is adjacent the topsheet in the second section 62, or the folded attachment panels 316 and 318 shown in FIG. 7. As a result, the backsheet of the first section 61 of the first portion 60 is exposed. Next, second portion 50 of the absorbent article 10 is folded along folding axes 42, such that the topsheet with the body adhesive 24 is adjacent the backsheet of the first section 61 of the absorbent article. The folded absorbent article is shown in FIG. 8.

As described above, other configurations of the absorbent article of the present invention may be folded in a similar manner. By folding the absorbent article as described above, such that the body adhesive contacts the backsheet of the first section 61 of the absorbent article, the backsheet may serve to protect the body adhesive present on the second portion, serving as a release strip. If this method of folding is used, the portion of the backsheet which comes into contact with the body adhesive may be treated with a release agent, so that the body adhesive contacts the release coating. Any suitable release coating, known to those skilled in the art may be used. By folding the absorbent article with a body adhesive applied to the second portion of the top sheet, the need for a release strip to cover and protect the body adhesive is not needed, thereby saving the cost of using the release strip and the use of natural resources needed to produce the release strip.

Figure 9:
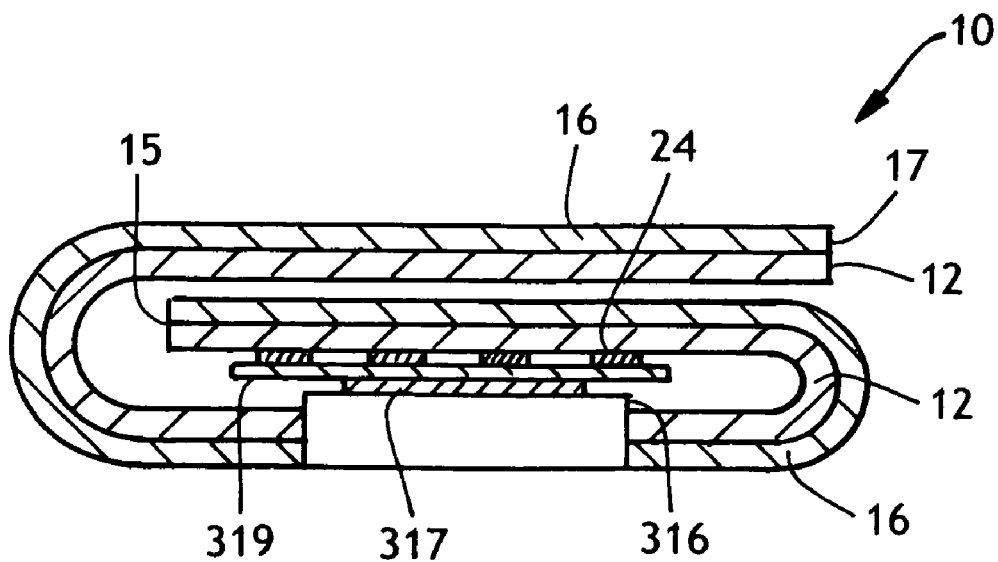
FIG. 9 shows a side view of an exemplary absorbent article of the present invention in a different tri-folded configuration.

In an alternative embodiment, when the garment attachment device is a garment adhesive applied to the backsheet of the first portion, the release strip of the back sheet may also serve as a release strip for the body adhesive when the absorbent article is tri-folded as shown in FIGS. 6-8. In this embodiment, it may be beneficial that both sides of the release strip are coated with a release coating so that the body adhesive does not transfer to the release strip. Likewise, if the garment attachment device is a pair of garment attachment panels which have an adhesive to hold the panels to the panty of a user, the garment attachment panels may first be folded onto the top sheet as shown in FIG. 7 and have a double sided release liner 319 placed on the garment adhesive patches 317 of the garment attachment panels. This would allow the second end 15, which is the longitudinal end of the second portion 50, to be first folded along fold axes 42 such that the topsheet in the second portion 50 is adjacent and the body adhesive 24 thereon is to be placed into contact with the second side of the release liner 319, placed on the garment adhesive 317 on the garment attachment panels. This is shown in FIG. 9. Then the first end 17 may be folded over such that the top sheet 12 of the first section 61 would be adjacent the backsheet 16 of the second portion 50. Other folding methods may also be used, which would be apparent to those skilled in the art.

Another advantage of having the body adhesive on the second portion of the absorbent article is that the adhesive can serve to prevent leaks from the absorbent article creating a dam-like structure with the skin of the user. In use, the second portion of the absorbent article may be lower than the first portion, especially when the user is lying down, such as while sleeping. As a result, the second portion of the absorbent article is the part of the absorbent article which will tend to leak, if a leak occurs. The body adhesive of the present invention may help prevent leaking from the second portion of the absorbent article. An additional advantage of the present invention is when the garment attachment is an attachment panel, the only additional attachment needed is an attachment device in the second portion of the absorbent article. Having a body adhesive in the second portion of the topsheet of the absorbent article has been found to be sufficient to hold the absorbent article in place during use. Unlike the prior body adhesive containing absorbent articles, the body adhesive absorbent articles of the present invention allow the user the convenience of using the garment attachment device to place the absorbent article in the panty, providing body adhesive at a location where it is most needed. This will allow a user to remove the panty and the absorbent article at the same time so that bodily functions can be performed without the need of having to remove the absorbent article from the body. As a result, by having the body adhesive in select portions of the absorbent article, the absorbent article of the present invention is as easy to use as an absorbent article without body adhesive, but provides the user the added protection provided by the body adhesive, as is explained above.

Figure 10:
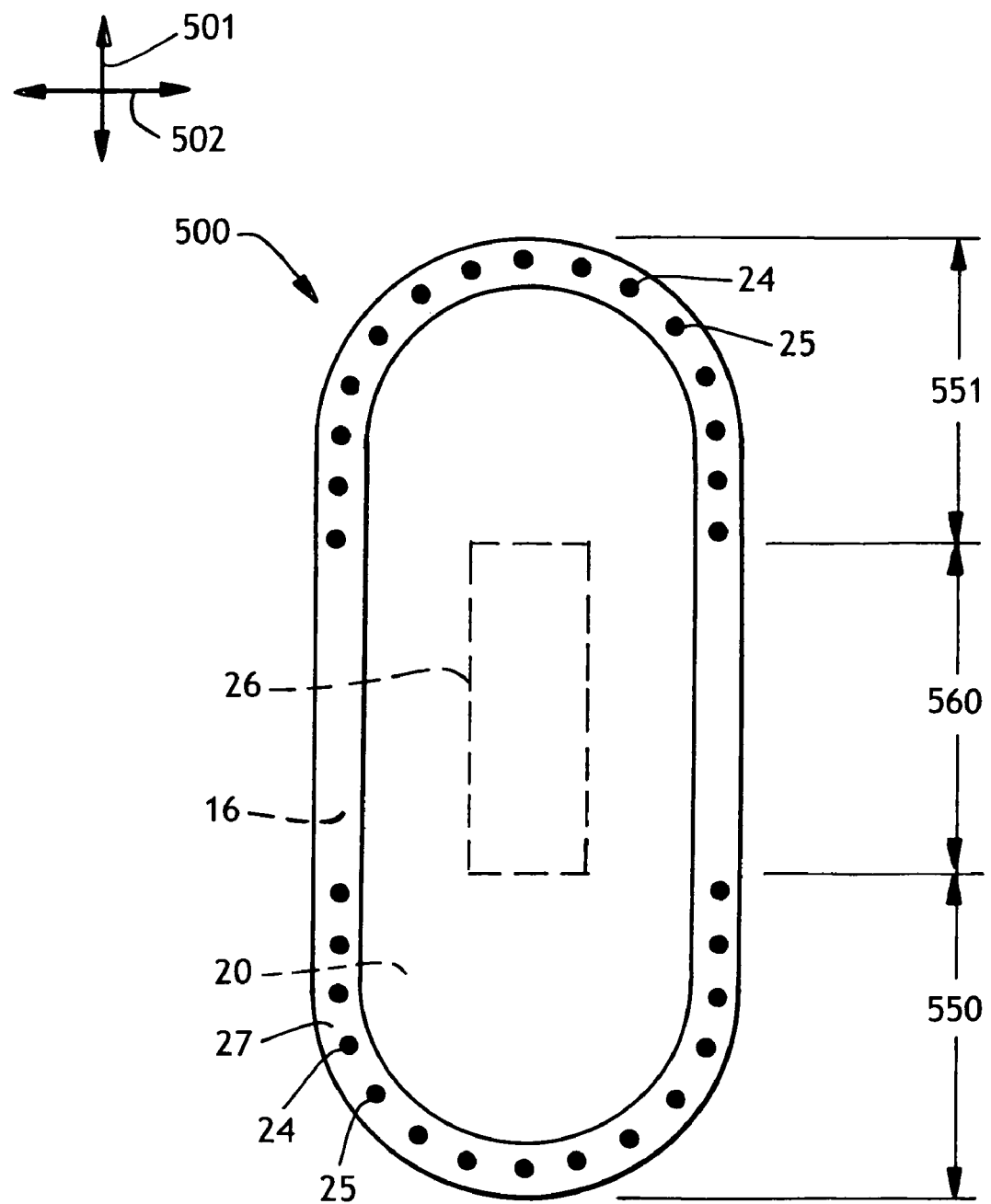
FIG. 10 shows a top view of another exemplary absorbent article of the present invention.

In an additional embodiment of the present invention as shown in FIG. 10, provided is an absorbent article 500 having longitudinal direction 501, a lateral direction 502, a first end portion 550, a second end portion 551 and an intermediate portion 560, the intermediate portion 560 joining the first end portion 550 to the second end portion 560. In this embodiment of the present invention, the absorbent article 500 has a topsheet 12 having a first major surface 14 which forms a body-facing surface of the absorbent article. In addition, the absorbent article has a backsheet 16 having a second major surface 18 disposed distally from said first major surface which forms a garment-facing surface of the absorbent article. On the first end portion 550 and the second end portion 551 of the topsheet 12 on the first major surface 14, a body adhesive 24 is applied. In the intermediate portion 560 of the absorbent article 500, a garment attachment device 26 for attaching the absorbent article to an undergarment of a user of the absorbent article is present.

In this additional embodiment of the present invention, the body adhesive 24 is essentially confined to the first and second end portions 550 and 551 of the absorbent article 500. By "essentially confined to the first and second end portions" it is intended that the majority of the body adhesive is located on the first and second end portions of the absorbent article. Stated another way, the body adhesive 24 may be present on the intermediate portion 560, but the majority of the body adhesive is present on the second portion of the absorbent article. In this embodiment of the present invention, ideally the body adhesive is not present on the intermediate portion 560 of the absorbent article 500, or if it is present, it is only present in very small amounts compared to the amounts of the body adhesive present on the first and second end portions. In one particular embodiment of the present invention, intermediate portion 560 of the absorbent article on the body-facing surface is essentially free of any body adhesive. In another embodiment, the intermediate portion 560 is substantially free of the body adhesive and desirably devoid of the body adhesive.

As with the other embodiment of the present invention where the body adhesive is applied to one portion of the absorbent article, the body adhesive absorbent articles of the present invention allow the user the convenience of using the garment attachment device to place the absorbent article in the panty, which provides body adhesive at a location where it is most needed. This will allow a user to remove the panty and the absorbent article at the same time so that bodily functions can be performed without the need of having to remove the absorbent article from the body. As a result, by having the body adhesive in select portions of the absorbent article, the absorbent article of the present invention is as easy to use as an absorbent article without body adhesive, but provides the user the added protection provided by the body adhesive, as is explained above. In addition, by having the body adhesive on both ends of the absorbent article, a user does not have to decide which is the front or back of the absorbent article, while providing leakage protection on both ends of the absorbent article.

The absorbent article of the present invention allow the consumer or user of the absorbent article to apply the absorbent article with the body adhesive, the garment attachment mechanism or both the body adhesive and the garment attachment mechanism. As a result the present invention provides a method of providing a consumer with a choice of how to apply an absorbent article for use. The method includes providing an absorbent article of the present invention having both a garment attachment mechanism and a body adhesive. In the method instructions are also provided to the consumer on how to apply the absorbent article with the body adhesive, and the garment attachment mechanism or a combination of the body adhesive and garment attachment mechanism.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. An absorbent article having a longitudinal direction, a lateral direction, a longitudinal length, a first portion and a second portion wherein the second portion is continuous and is no greater than 50% of the longitudinal length and the first portion is continuous and is the remainder of the longitudinal length, the absorbent article comprising:

a liquid permeable topsheet having a first major surface which is adapted to form a body-facing surface;

a liquid impermeable backsheet having a second major surface which is adapted to form a garment-facing surface;

an absorbent core positioned between the backsheet and the topsheet;

a body adhesive applied to the topsheet in the second portion of the absorbent article; and a garment attachment device being applied to or attached to the second major surface and being present in only the first portion of the absorbent article;

wherein the topsheet is substantially free of any body adhesive in the first portion of the absorbent article.

2. The absorbent article according to claim 1, wherein the second portion consists of 10% to 50% of the longitudinal length of the absorbent article and the first portion consists of 50% to 90% of the longitudinal length of the absorbent article.

3. The absorbent article according to claim 2, wherein the first portion of the absorbent article is divided into a first section and a second section, wherein the second section is proximate to the second portion, each of the first section and the second section have a length in the longitudinal direction, the length of the second section being equal to or greater than the length of the first section, the absorbent article being tri-folded such that the first section is folded over onto the second section such that the topsheet of the first section and the topsheet of the second section are in a direct or indirect face to face relationship to one another exposing the backsheet of the first section, and the second portion is folded onto the backsheet of the first section such that the body adhesive present on the second portion is in contact with the backsheet of the first section.

4. The absorbent article according to claim 1, wherein the second portion comprises ⅓ of the longitudinal length of the absorbent article and the first portion comprises ⅔ of the longitudinal length of the absorbent article.

5. The absorbent article according to claim 1, wherein the absorbent article further comprises longitudinal side edges and the garment attachment device comprises an adhesive applied to the backsheet, a mechanical attachment system applied to the backsheet, attachment panels extending from each longitudinal side edges, attachment panels attached to the backsheet, or a combination thereof.

6. The absorbent article according to claim 1, wherein the body adhesive is a pressure sensitive adhesive.

7. The absorbent article of claim 1, wherein the first portion of the absorbent article is divided into a first section and a second section, wherein the second section is proximate to the second portion, each of the first section and the second section have a length in the longitudinal direction, the length of the second section being equal to or greater than the length of the first section, the absorbent article being tri-folded such that the first section is folded over onto the second section and the topsheet of the first section and the topsheet of the second section are in a direct or indirect face to face relationship to one another exposing the backsheet of the first section, the second portion is folded onto the backsheet of the first section such that the body adhesive present on the second portion is in contact with the backsheet of the first section.

8. The absorbent article according to claim 1, wherein the topsheet and the back-sheet are extensible.

9. The absorbent article according to claim 1, wherein the topsheet, the backsheet and the absorbent core are extensible.

\* \* \* \* \*